(12) United States Patent
Shih

(10) Patent No.: US 10,781,120 B2
(45) Date of Patent: Sep. 22, 2020

(54) HEATERLESS HYDROLYTIC DEGRITTER

(71) Applicant: Holistic Farming, Inc. (HFI), Cary, NC (US)

(72) Inventor: Jason Chia Hsing Shih, Cary, NC (US)

(73) Assignee: Holistic Farming, Inc (HFI), Cary, NC (US)

( * ) Notice: Subject to any disclaimer, the term of this patent is extended or adjusted under 35 U.S.C. 154(b) by 0 days.

(21) Appl. No.: 16/431,434

(22) Filed: Jun. 4, 2019

(65) Prior Publication Data
US 2019/0284070 A1    Sep. 19, 2019

Related U.S. Application Data

(63) Continuation-in-part of application No. 13/793,140, filed on Mar. 11, 2013, now abandoned.

(51) Int. Cl.
| | | |
|---|---|---|
| C02F 3/28 | (2006.01) | |
| C12M 1/00 | (2006.01) | |
| C05F 3/00 | (2006.01) | |
| C05F 17/40 | (2020.01) | |
| C02F 103/20 | (2006.01) | |
| C12M 1/107 | (2006.01) | |
| C05F 17/50 | (2020.01) | |

(52) U.S. Cl.
CPC ............... *C02F 3/286* (2013.01); *C05F 3/00* (2013.01); *C05F 17/40* (2020.01); *C12M 45/04* (2013.01); *C12M 45/06* (2013.01); *C02F 2103/20* (2013.01); *C05F 17/50* (2020.01); *C12M 21/04* (2013.01); *Y02A 40/205* (2018.01); *Y02P 20/145* (2015.11); *Y02W 30/43* (2015.05); *Y02W 30/47* (2015.05)

(58) Field of Classification Search
CPC ...... Y02E 50/343; C02F 3/28; C02F 2103/20; C05F 17/40; C05F 17/60; B01D 21/0006; B01D 21/00; B09B 3/00
USPC ............. 210/803; 209/172.5, 173, 172
See application file for complete search history.

(56) References Cited

U.S. PATENT DOCUMENTS

| | | |
|---|---|---|
| 4,040,953 A | 8/1977 | Ort |
| 4,372,856 A | 2/1983 | Morrison |
| 5,525,229 A | 6/1996 | Shih |
| 7,081,199 B2 | 7/2006 | Leskow |
| 7,179,642 B2 | 2/2007 | Dvorak |
| 7,306,731 B1 | 12/2007 | Dewaard |
| 2010/0173391 A1* | 7/2010 | Dvorak ............... C05F 17/40 435/262.5 |
| 2012/0055861 A1 | 3/2012 | Conwell |

FOREIGN PATENT DOCUMENTS

| | | |
|---|---|---|
| CA | 576500 A | 5/1959 |
| GB | 1437336 | 5/1976 |

* cited by examiner

*Primary Examiner* — Claire A Norris
(74) *Attorney, Agent, or Firm* — James G. Passé; Passé Intellectual Property, LLC

(57) ABSTRACT

The present invention relates to improving the results of anaerobic digestion of organic waste especially animal manure such as chicken manure by removing the grit in the waste by digesting the waste in a slurry at a temperature of about 50° C. or more for a period of time sufficient for the grit to settle out of the slurry.

5 Claims, 2 Drawing Sheets

HEATERLESS HYDROLYTIC DEGRITTER

This application is a continuation-in-part of U.S. non-provisional application Ser. No. 13/793,140 filed on Mar. 11, 2013, and which is incorporated herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to a system and method for the degritting of waste, such as animal waste, in a hydrolytic system. In particular, it relates to a low energy waste digestion at incubation temperatures which causes grit to settle out of the incubation slurry without an internal heater in the digestion tank.

Description of Related Art

The anaerobic digestion of organic material such as sewage sludge, municipal waste, industrial waste, forest waste, agricultural waste, and especially animal waste is the fermentation of such material by bacteria in the absence of oxygen. The benefit of such digestion of waste material includes the stabilization of waste, odor control, solid reduction, energy production in the form of methane gas, elimination or reduction of pathogens, making the waste more environmentally neutral, production of a nutrient source, and the like. Generally, it has been used in many large scale treatments of animal wastes to control the disposal problem associated with such waste.

Animal feed, in particular poultry feed, typically has a large amount of insoluble grit material such as limestone, sands, or shells material added to improve the feed for food grinding in the gizzard and to supplement calcium to the animal. The insoluble grit becomes a large problem when delivered to an anaerobic digester for biogas production. The grit can clog up the feed lines and fill up the internal space of the digester. It tends to be abrasive as well and can easily damage equipment. The removal of such grit is highly desirable.

BRIEF SUMMARY OF THE INVENTION

The present invention relates to the discovery that grit can easily and cost effectively be removed from waste material such as poultry waste. The process involves hot water and waste being combined and mixed at elevated temperatures in an unheated, insulated tank allowing all the grit to settle to the bottom of the tank for separation without the cost or problems of a heater in the tank.

Accordingly, in one embodiment, the present invention relates to a low energy method of separating grit from animal manure before placement in a digester consisting of:

a) adding animal manure and heated water either separately or together to a top of an upright, unheated, insulated upright tank with a top and bottom consisting of a mixing apparatus and insulation, and wherein the tank is designed to separate grit from the tank;

b) wherein the water is of sufficient elevated temperature to obtain an elevated temperature slurry mixture of the water and manure of at least about 50° C., and of a solids content of about 12% or less, wherein the tank is insulated sufficiently to maintain the elevated temperature of at least about 50° C. to about 60° C. created from adding the heated water during the method, wherein the insulated tank does not have a heater, and wherein the tank is closed during the grit separation;

c) mixing the contents of the insulated tank with the mixing apparatus for a period of 18 to 24 hours at the elevated temperature of at least about 50° C. such that the grit settles to the bottom of the tank; and d) separating the settled grit from the remaining slurry in the tank.

DETAILED DESCRIPTION OF THE INVENTION

Figure 1:
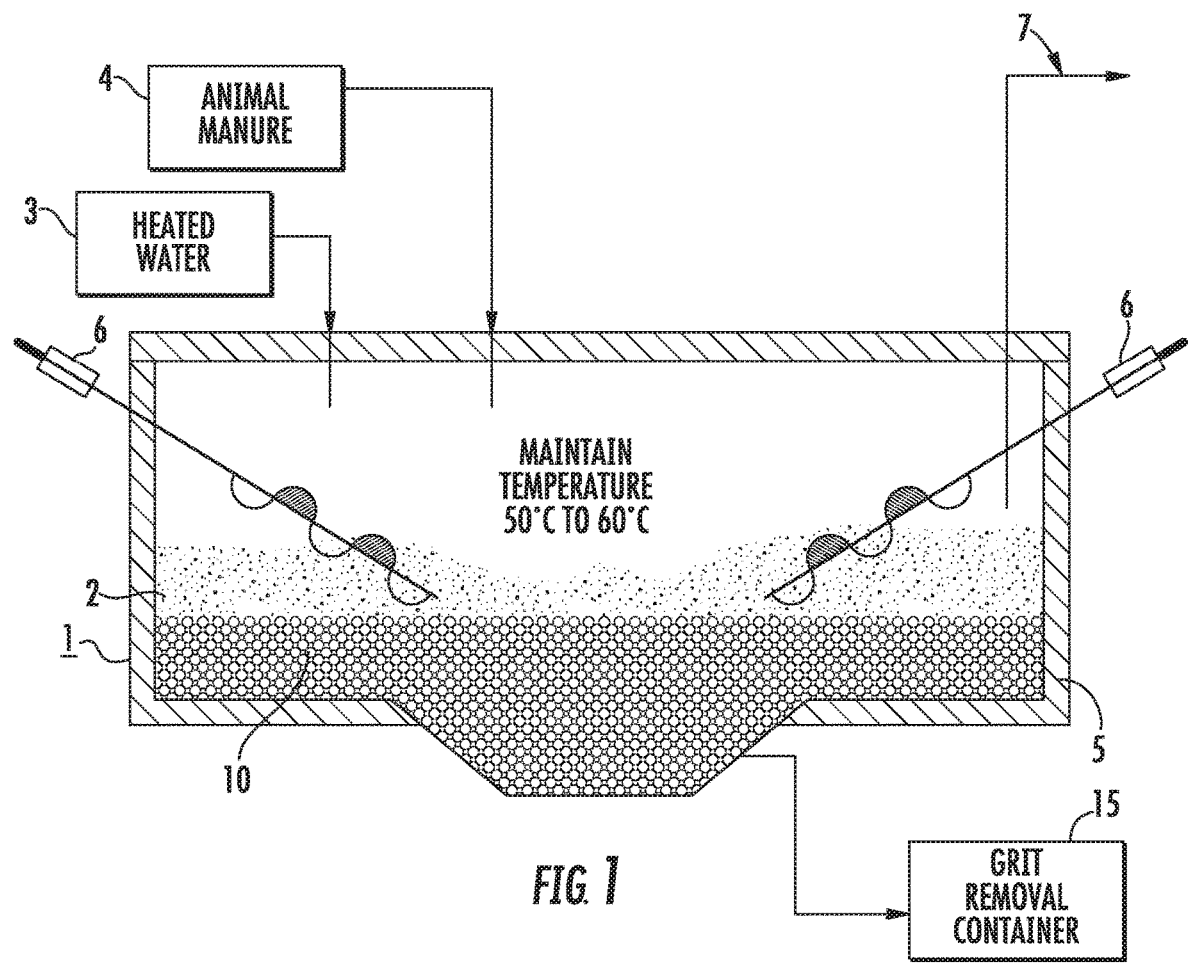
FIG. 1 is a perspective view of a hydrolytic degritter of the present invention.

While this invention is susceptible to embodiment in many different forms, there is shown in the drawings, and will herein be described in detail, specific embodiments with the understanding that the present disclosure of such embodiments is to be considered as an example of the principles and not intended to limit the invention to the specific embodiments shown and described. In the description below, like reference numerals are used to describe the same, similar, or corresponding parts in the several views of the drawings. This detailed description defines the meaning of the terms used herein and specifically describes embodiments in order for those skilled in the art to practice the invention.

DEFINITIONS

The terms "about" and "essentially" mean ±10 percent.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment", "certain embodiments", "an embodiment", or similar terms means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner in one or more embodiments without limitation.

The term "or", as used herein, is to be interpreted as an inclusive or meaning any one or any combination. Therefore, "A, B, or C" means any of the following: "A; B; C; A and B; A and C; B and C; A, B, and C". An exception to this definition will occur only when a combination of elements, functions, steps, or acts are in some way inherently mutually exclusive.

The drawings featured in the figures are for the purpose of illustrating certain convenient embodiments of the present invention and are not to be considered as limitation thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein, and use of the term "means" is not intended to be limiting.

As used herein, the term "grit" refers to insoluble matter that exists within organic waste like animal manure. This includes, in one embodiment, the solid material found in animal waste such as described above. The term "organic waste" refers to any of the waste type materials described above which would be used in an anaerobic digestion system and containing grit. In one embodiment, the organic waste is animal manure. In another embodiment, it is chicken manure.

As used herein, the term "tank" refers to an unheated, insulated tank designed for holding organic waste and mixing at an elevated temperature of at least about 50° C. The tank can be made of any material such as stainless steel and the tank is insulated to better hold the elevated temperature since there is no heater in the tank itself. The tank is fitted on the interior with a mixing apparatus to keep the contents of the tank mixing during the process of the invention. One skilled in the art could choose an appropriate mixing apparatus. Heating is conducted before addition of heated water to the tank. Since the grit needs to be removed and eventually ends up on the bottom of the tank after the process, the tank can be fitted with a pump to remove the grit or remaining slurry, or with a bottom drain such as conical area, to remove the grit by bleeding off the grit. The degritted slurry is transferred by pump into the anaerobic digester. Water is heated prior to putting it in the tank. The water is of sufficiently high temperature to obtain a slurry of manure and heated water at a temperature of at least about 50° C. during the mixing process. In one embodiment, the mixing process takes about 18 to 24 hours. In one embodiment, the temperature reaches at least 60° C. The heated water and manure are not mixed until in the tank. No additional heat is used after the process is started.

The tank or system is emptied, typically daily, for the second batch of hydrolysis.

The method of the present invention involves adding the organic waste such as animal manure (chicken manure) to the tank. Water is heated and added to the tank to obtain a lower solids slurry mixture. In general, one skilled in the art can obtain the optimum percentage of solids, and thus the proper amount of heated water based on the weight of the manure added by simple testing of the process. In one embodiment, the percent solids in the manure is 10% to 20% on a weight/weight basis prior to water addition. In other embodiments, it can be 10% or less solids and can, in some circumstances, be higher than 20%. In general, the degritter process takes about a day however, it depends on the concentration of grit. The water and manure slurry after water addition, in one embodiment, is about 5%-10% solids, in another embodiment, less than 5% solids.

The contents of the tank need to be kept at a temperature of at least about 50° C. during the method of the present invention. The tank needs to be insulated sufficiently to maintain temperature during the process. The water and/or manure can be preheated to a temperature that maintains at least about 50° C. during the process before addition to the tank. In one embodiment, the temperature is kept within about 50° C. to about 60° C. for a period sufficient to settle out essentially all the grit from the slurry. The sufficient time, as used herein, will vary depending on the organic material and ambient conditions, the size of the tank, and the like, but in one embodiment, the time is about 18 to 24 hours. One skilled in the art could readily determine the amount of time and water temperature based on the teachings herein and with minimal experimentation.

Once the slurry is degritted, it can be delivered to an anaerobic digester for productivity of biogas and fertilizer. Also, it can be further digested in a novel secondary solid as described in, for example, SECONDARY SOLID-PHASE ANAEROBIC DIGESTION PRODUCING MORE BIOGAS issued as U.S. Pat. No. 9,242,881 on Jan. 26, 2016 in the name of Jason Chia Hsing Shih.

Now referring to the figures, the following FIG. 1 depicts an embodiment of the hydrolytic degritter system of the present invention. In this view, hydrolytic degritter insulated tank 1 is shown with tank slurry 2 which is made from the addition of heated water 3 and animal manure 4 from containers/pipelines/faucets, and the like. Once the proper low solids slurry is formed, it is kept heated by insulation 5 and then kept in a state of constant mixing using mixer 6. In this embodiment, an 8-12% solids content slurry is utilized.

FIG. 1 shows the process with grit 10 settling out at the bottom of tank 1. In reality, the solids would settle out after the process but is shown in this manner for convenience. In this embodiment, grit 10 can be removed from hydrolytic degritter insulated tank 1 by bleeding the grit into grit removal container 15. The grit 10 in grit removal container 15 can be washed and that washed grit returned to the hydrolytic degritter insulated tank 1. The tank slurry 2 minus the grit 10 is transferred 7 to an anaerobic digester for production of biogas and fertilized over a period of 5-10 days. Though one skilled in the art can determine optimum times.

Figure 2:
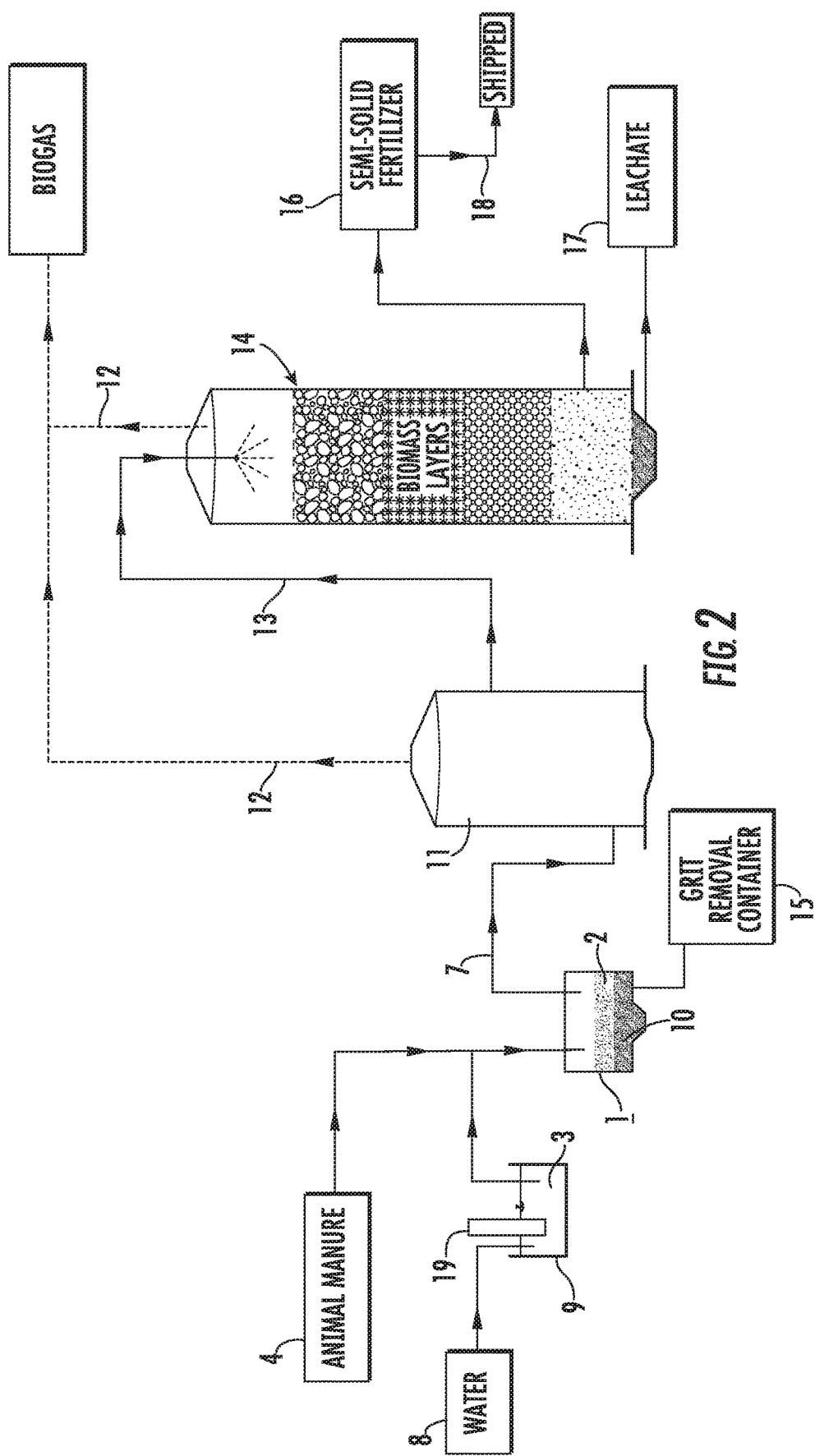
FIG. 2 is a view of the hydrolytic degritter in a biogas/fertilizer production system. In this embodiment, the hydrolytic degritter system has a heated water tank.

FIG. 2 shows the hydrolytic degritter in a system for degritting and digesting the manure into biogas and solid material slurry which can be used for fertilizer and other uses. In one embodiment, water 8 is added to water tank 9 and heated with heater 19. In one embodiment, the heated water 3 is mixed with animal manure 4 and added to hydrolytic degritter insulated tank 1. The slurry material is transferred 7 to the primary anaerobic digester 11. The slurry is digested for about 5-10 days, or as needed, to produce biogas 12 and a solid slurry about 2-5% solids 13. The solids 13 are delivered to a secondary solid phase digester 14 for further biogas production and a semi-solid slurry which can be utilized as fertilizer 16 and a leachate 17. In one embodiment, the fertilizer is shipped 18 to users.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials, and the like apparent to those skilled in the art still fall within the scope of the invention as claimed by the applicant.

What is claimed is:

1. A low energy method of separating grit from animal manure before placement in a digester consisting of:
   a) adding animal manure and heated water either separately or together to a top of an upright, unheated, insulated upright tank with a top and bottom consisting of a mixing apparatus and insulation, and wherein the tank is designed to separate grit from the tank;
   b) wherein the water is of sufficient elevated temperature to obtain an elevated temperature slurry mixture of the water and manure of at least about 50° C., wherein the tank is insulated sufficiently to maintain the elevated temperature of at least about 50° C. to about 60° C. created from adding the heated water during the method, wherein the insulated tank does not have a heater, and wherein the tank is closed during the grit separation;
   c) mixing the contents of the insulated tank with the mixing apparatus for a period of 18 to 24 hours at the elevated temperature of at least about 50° C. such that the grit settles to the bottom of the tank; and
   d) separating the settled grit from the remaining slurry in the tank.

2. The method according to claim 1 wherein the water and manure slurry before grit removal has about 5% to 10% solids.

3. The method according to claim 1 wherein the grit is removed by at least one of pumping or bleeding off from the bottom of the tank.

4. The method according to claim 1 wherein the organic raw waste is raw animal manure.

5. The method according to claim 4 wherein the manure is chicken manure.

* * * * *